US007259232B1

(12) United States Patent
Fitzpatrick et al.

(10) Patent No.: US 7,259,232 B1
(45) Date of Patent: Aug. 21, 2007

(54) PREFERRED SEGMENTS OF NEURAL THREAD PROTEIN

(75) Inventors: Judith Fitzpatrick, Englewood, NJ (US); Paul Averback, St. Laurent (CA); Maggie Focht, Glen Rock, NJ (US); Riza Bibiano, Old Bridge, NJ (US)

(73) Assignee: Nymox Pharmaceutical Corporation, Quebec (CA)

( * ) Notice: Subject to any disclaimer, the term of this patent is extended or adjusted under 35 U.S.C. 154(b) by 0 days.

(21) Appl. No.: 09/697,590

(22) Filed: Oct. 27, 2000

(51) Int. Cl.
C07K 14/435 (2006.01)
C07K 5/04 (2006.01)
(52) U.S. Cl. ..................................... 530/300; 530/330
(58) Field of Classification Search ................ 435/7.1; 531/350; 530/350
See application file for complete search history.

(56) References Cited

U.S. PATENT DOCUMENTS

| 4,816,567 A | 3/1989 | Cabilly et al. ............... 530/387 |
| 5,084,559 A | 1/1992 | Profy ......................... 530/387 |
| 5,100,788 A | 3/1992 | Lofdahl et al. ............. 435/69.7 |
| 5,830,670 A * | 11/1998 | de la Monte et al. ......... 435/7.2 |
| 5,834,287 A * | 11/1998 | Kubota et al. ............... 435/201 |
| 5,948,634 A | 9/1999 | De la Monte et al. ...... 435/69.1 |
| 6,013,763 A | 1/2000 | Braisted et al. ............. 530/317 |
| 6,610,506 B1 * | 8/2003 | Lo et al. .................... 435/69.1 |

FOREIGN PATENT DOCUMENTS

| EP | 0 068 375 A2 | 1/1983 |
| WO | 90/06993 | 6/1990 |
| WO | WO 96/14334 | 5/1996 |
| WO | WO96/18646 A2 | 6/1996 |
| WO | WO99/16710 A1 | 4/1999 |
| WO | WO 00/01720 A2 | 1/2000 |
| WO | WO 00/55198 A1 | 9/2000 |
| WO | WO 00/58495 A1 | 10/2000 |
| WO | WO 02/092115 A2 | 11/2002 |

OTHER PUBLICATIONS

Rosen et al., WO 00/55199 published Sep. 21, 2000, p. 1 and 74, SEQ ID No. 123.*
Motter et al., "Reduction of β-Amyloid Peptide$_{42}$ in the Cerebrospinal Fluid of patients with Alzheimer's Disease", Annals of Neurology, 38(4):643-648, (1995), Amer. Neurological Assoc.
Molsa et al., "Validity of clinical diagnosis in dementia: a prospective clinicopathological study", J. Neuro. & Psych, 48:1085-1090, (1985), British Medical Assoc.
Rocca et al. "Epidemiology of Clinically Diagnosed Alzheimer's Disease", Ann. Neurol 19:415-424, (1986), Nat'l. Inst. Of Health.
Burns et al. "Accuracy of clinical diagnosis of Alzheimer's disease", 301:1026, (1990), Inst. Of Psychiatry.
Risse et al., "Neuropathological findings in patients with clinical diagnoses of probable alzheimer's disease", Am. J. Psychiatry 147(2):168-172, (1990), Amer. Psychiatric Assoc.

Gilleard et al., "The St. George's dementia bed investigation study: a comparison of clinical and pathological Diagnosis", Acta Psychiatrica Scandinavica, 85(4):264-269, 1992, Dept. of Geriatric Medicine.
Mendez et al., "Clinically diagnosed Alzheimer Disease: Neuropathologic findings in 650 Cases", Alzheimer Disease and Assoc. Disorders, 6(1):35-43, 1992, Raven Press, Ltd.
Fleming et al., "Dementia: Diagnosis and Evaluation", Mayo Clin. Proc. 70:1093-1107, (1995), Mayo Foundtn. For Medical Education Research.
Bloom et al., "Diagnosis and evaluation of dementia", Neurology 45:211-218, (1995), Amer. Academy of Neurology.
Bowler et al., "Fallacies in the pathological confirmation of the diagnosis of Alzheimer's disease", Neurol. Neurosurg Psychiatry, 64:18-24, (1998), BMJ Publishing Group.
Jost et al. "The natural History of Alzheimer's Disease: A Brian Bank Study", JAGS 43:1248-1255, (1995) The American Geriatrics Society.
Growdon et al., Ronald & Nancy Reagan "Consensus report of the working group on: Molecular and Biochemical Markers of Alzheimer's Disease", Neurobiology of Aging, 19(2):109-116, (1998), Elsevier Sci. Inc.
Myers et al., "Apolipoprotein E ε4 association with dementia in a population-based study", Neurology 46:673-677, 1996, American Academy of Neurology.
Pirttila et al., "Soluble amyloid β-protein in the cerebrospinal fluid from patients with Alzheimer's disease, Vascular dementia and controls", J. of Neurological Sciences, 127:90-95, (1994), Elsevier Science B.V.
Arai et al., "Tau in Cerebrospinal Fluid: A potential diagnostic marker in Alzheimer's Disease", Ann. Neurol. 38:649-652, (1995), Amer. Neurological Assoc.
Jensen et al., "Increased cerebrospinal fluid tau in patients with Alzheimer's disease", Neuroscience Letters, 186:189-191, (1995), Elsevier Science Ireland Ltd.
Munroe et al., "Tau Protein in Cerebrospinal Fluid as an Aid in the Diagnosis of Alzheimer's Disease" Annals of Clinical & Laboratory Science, 25(3):207-217, (1995), Inst. For Clinical Science, Inc.
Tato et al., "Tau protein concentrations in cerebrospinal fluid of patients with dementia of the Alzheimer type", J. of Neurology, Neurosurgery, & Physchiatry, 59(3):280-283 (1995), BMJ Publishing Group.
T. Iwatsubo, "Amyloid β Protein in Plasma as a Diagnostic marker for Alzheimer's Disease", Neurobiology of Aging, 19(2):161-163, (1998), Elsevier Science Inc.

(Continued)

Primary Examiner—Elizabeth Kemmerer
Assistant Examiner—Kimberly A. Ballard
(74) Attorney, Agent, or Firm—Foley & Lardner LLP

(57) ABSTRACT

The invention is directed to preferred repeat sequences of Neural Thread Protein (NTP), peptides, mimetics, antibodies, and nucleic acids of the preferred sequences, and diagnostic and therapeutic methods of using such preferred NTP sequences.

3 Claims, 6 Drawing Sheets

OTHER PUBLICATIONS

Vigo-Pelfrey et al., "Elevation of microtubule-associated protein tau in the cerebrospinal fluid of patients with Alzheimer's disease", Neurology 45:788-793, (1995), Advanstar Communications inc.

Nitsch et al., "Cerebrospinal fluid levels of Amyloid β-Protein in Alzheimer's disease: Inverse correlation with Severity of Dementia and effect of Apolipoprotein E Genotype", Annals of Neurology, 37(4):512-518, (1995) American Neurological Association.

Van Gool et al., "Concentrations of Amyloid β protein in cerebrospinal fluid of patients with Alzheimer's Disease", Annals of Neurology, 37(2):277-279, (1995), American Neurological Association.

Matsuura et al., "Autosomal dominant spastic paraplegia linked to chromosome 2p: clinical and genetic studies Of a large Japanese pedigree", J. of Neurological Sciences, 151:65-70, (1997), Elsevier Science B.V.

Pirttila et al., "Cerebrospinal fluid concentrations of soluble Amyloid β-protein and apoliporotein E in patients With Alzheimer's disease", Arch. Neurol. 53:189-193, (1996), American Medical Association.

Scinto et al., "A Ptential noninvasive neurobiological test for Alzheimer's disease", Science 266:1051-1054 (1994), American Association for the Advancement of Science.

Growdon et al., "Pupil dilation tropicamide is not specific for Alzheimer's disease", Arch Neirol. 54:841-844 (1997), American Medical Association.

Kennard et al., "Serum levels for the iron binding protein p97 are elevated in Alzheimer's disease", Nature Medicine, 2(11):1230-1235 (1996), National Library of Medicine.

De la Monte et al., "Characterization of the AD7C-NTP cDNA Expression in Alzheimer's Disease and Measurement of a 41-kD protein in Cerebrospinal fluid", J. Clin. Invest. 100(12):3093-3104, (1997) American Society for Clinical Investigation, Inc.

De la Monte et al., "AD7c-NTP biomarker for Alzheimer's disease", Alzheimer's Reports 2(6):327-332, (1999) National Library of Medicine.

Ozturke et al., "Elevated levels of an exocrine pancreatic secretory protein in Alzheimer disease brain", Proc. Nat'l. Acad. Sci., 86:419-423, (1989), Molecular Hepatology Laboratory.

De la Monte et al., "Enhanced expression of an Exocrine pancreatice protein in Alzheimer's disease and the Developing human brain", J. Clin. Invest., 86:1004-1013, (1990), Amer. Society for Clinical Invest. Inc.

De la Monte et al., "Increased levels of Neuronal thread protein in cerebrospinal fluid of patients with Alzheimer's disease", Ann Neurol 32(6):733-742 (1992), Amer. Neurological Assoc.

De la Monte et al., "Profiles of Neuronal thread protein expression in Alzheimer's disease", J. Neuro. & Experimental Neurology, 55(10):1038-1050, (1996), American Assoc. of Neuropathologies.

De la Monte et al. "Modulation of neuronal thread protein expression with neuritic sprouting: relevance to Alzheimer's disease", J. of Neurological Sciences 138:26-35, (1996), Elsevier Science B.V.

De la Monte et al., "Developmental patterns of neuronal thread protein gene expression in down syndrome", J. of Neurological Sciences, 135:118-125, (1996), Elsevier Science B.V.

Chong et al., "Automated Microparticle Enzyme Immunoassay for Neural thread protein in cerebrospinal Fluid from Alzheimer's disease patients", J. Clinical Lab. Analysis, A;379-383 (1992), Wiley-Liss, Inc.

Ghanbari et al., "A sandwich enzyme immunoassay for measuring AD7C-NTP as an Alzheimer's Disease Marker: AD7C Test", J. of Clinical Lab. Analysis 12:223-226 (1998), Wiley-Liss Inc.

HosseinGhanbari et al., Specificity of AD7C-NTPasaBiochemical Marker for Alzheimer's disease, J. of Contemporary Neurology, 1998(4A):2-7, (1998), Massachusetts institute of Technology.

Kahle et al., "Combined assessment of tau and neuronal thread protein in Alzheimer's disease CSF", Neuro. 54:1498-1504, (2000), American Academy of Neurology.

Ghanbari et al., "Biochemical Assay for AD7C-NTP in Urine as an Alzheimer's Disease Marker", J. of Clin. Lab. Analysis 12:285-288 (1998), Wiley-Liss, Inc.

Fitzpatrick et al., "7C Gold urinary assay of neural thread protein in Alzheimer's disease", Alzheimer's Reports 3(3):155-159 (2000), MSJ.

G. von Heijne, "Sequence Similarities Homologies, and Alignments", Sequence Analysis in Molecular Biology, pp. 123-139 (1987), Academic Press, Inc.

Wikstrom et al., "Computer simulation of weak affinity chromatography", J. of Chromatography 597:83-92 (1992), Elsevier Science Publishers B.V.

Fassina et al., "Protein A mimetic peptide ligand for affinity purification of antibodies", J. of Molecular Recog. 9:564-569, (1996), John Wiley & Sons, Ltd.

Guerrier et al., "IRIS 97: an innovative protein A-peptidominetic solid phase medium for antibody purification", J. of Molecular Recognition, 11:107-109, (1998), John Wiley & Sons, Ltd.

Palombo et al., "A synthetic ligand for IgA affinity purification", J. of Molecular Recognition, 11:243-246 (1998) John Wiley & Sons, Ltd.

Palombo et al., "Affinity purification of mouse monoclonal IgE using a protein A mimetic ligand (TG19318) Immobilized on solid supports", J. of Molecular Recognition, 11:247-249 (1998) John Wiley & Sons, Ltd.

Braisted et al., "Minimizing a binding domain from protein A", Proc. Natl. Acad. Sci. 93(12):5688-5692, (1996) Univ of California @ Berkeley.

Fassina et al., "Immunoglobulin specificity of TG19318: a novel synthetic ligand for antibody affinity purification", J. of Molecular Recog. 11:128-133, (1998), John Wiley & Sons, Ltd.

Li et al., "Design, synthesis, and application of a Protein A mimetic", Nature Biotech. 16(2):190-195, (1998) National Library of Medicine.

Mayo, "Recent advances in the design and construction of synthetic peptides: for the love of basics or just for The Technology of it", TIBTECH 18:212-217, (2000), Elsevier Science Ltd.

Lacy et al., "Identification of FKRT1, FLRT2, and FLRT3: A novel Family of transmembrane leucine-rich Repeat proteins", Genomics 62:417-426, (1999), Academic press.

Snellman et al., "A short sequence in the N-terminal region is required for the trimerization of type XIII collagen And is conserved in other collagenous transmembrane proteins", The EMBO Journal, 19(19):5051-5059, 2000 European Molecular Biology Organization.

Koide et al., "Conformational requirements of collagenous peptides for recognition by the Chaperone Protein HSP47", J. of Biological Chemistry 275(36):27957-27963, (2000), Amer. Society for Biochem. & Mol. Bio. Inc.

Schittny, "Affinity retardatio chromatography: characterization of the method and its application", Analytical Biochemistry 222:140-148, (1994), Academic Press Inc.

Deisenhofer, "Crystallographic refinement and atomic models of a human Fc fragment and its complex with Fragment B of protein A from *Staphylococcus aureus* at 2.9- and 2.8-Å resolution", Biochemistry 20(9):2361-2370, (1981), American Chemical Society.

Serio et al., "Nucleated Conformational conversion and the replication of conformational information by a Prion Deteminant", Science 289(5483):1317-1321, (2000), American Assoc. for the Advancement of Science.

Sparrer et al., "Evidence for the prion hypothesis: induction of the yeast [PSI$^+$] factor by in vitro-converted Sup35 protein", Science 289(5479):497-684, (2000), American Assoc. for the Advancement of Science.

Kohler & Milstein, "Continuous cultures of fused cells secreting antibody of predefined specificity", Nature, , 256(5517):495-497 (1975), MRC Laboratory of Molecular Biology, UK.

Author Index, Journal of the Neurological Sciences, Oct. 22, 1997, vol. 151, No. 2, pp. 236-237.

Vasilakos et al., "Herpes Simplex Virus Class I-Restricted Peptide Induces Cytotoxic T Lymphocytes In Vivo Independent of CD4+ T Cells," *Journ. Of Immunolgy*, vol. 150, No. 6, 1993, pp. 2346-2355.

\* cited by examiner

Fig. 1

```
   1 tttttttttttgag ATG GAG TTT TCG CTC TTG TTG CCC AGG CTG GAG TGC AAT GGC GCA ATC  62
   1                 M   E   F   S   L   L   L   P   R   L   E   C   N   G   A   I   16
  63 TCA GCT CAC CGC AAC CTC CGC CTC CCG GGT TCA AGC GAT TCT CCT GCC TCA GCC TCC CCA 122
  17  S   A   H   R   N   L   R   L   P   G   S   S   D  (S)  P   A   S   A  (S)  P   36
 123 GTA GCT GGG ATT ACA GGC ATG TGC ACC CAC GCT CGG CTA ATT TTG TAT TTT TTT TTA GTA 182
  37  V   A   G   I   T   G   M   C   T   H   A   R   L   I   L   Y   F   F   L   V   56
 183 GAG ATG GAG TTT CTC CAT GTT GGT CAG GCT GGT CTC GAA CTC CCG ACC TCA GAT GAT CCC 242
  57  E   M   E   F   L   H   V   G   Q   A   G   L   E   L   P   T  (S)  D   D   P   76
 243 TCC GTC TCG GCC TCC CAA AGT GCT AGA TAC AGG ACT GGC CAC CAT GCC CGG CTC TGC CTG 302
  77 (S)  V  (S)  A   S   Q  (S)  A   R   Y   R  (T)  G   H   H   A   R   L   C   L   96
 303 GCT AAT TTT TGT GGT AGA AAC AGG GTT TCA CTG ATG TGC CCA AGC TGG TCT CCT GAG CTC 362
  97  A   N   F   C   G   R   N   R   V   S   L   M   C   P   S   W  (S)  P   E   L  116
 363 AAG CAG TCC ACC TGC CTC AGC CTC CCA AAG TGC TGG GAT TAC AGG CGT GCA GCC GTG CCT 422
 117  K   Q  (S)  T   C   L   S   L   P   K   C   W   D   Y   R   R   A   A   V   P  136
 423 GGC CTT TTT ATT TTA TTT TTT TTA AGA CAC AGG TGT CCC ACT CTT ACC CAG GAT GAA GTG 482
 137  G   L   F   I   L   F   F   L   R   H   R   C   P  (T)  L   T   Q   D   E   V  156
 483 CAG TGG TGT GAT CAC AGC TCA CTG CAG CCT TCA ACT CCT GAG ATC AAG CAT CCT CCT GCC 542
 157  Q   W   C   D   H   S   S   L   Q   P  (S)  T   P   E   I   K   H   P   P   A  176
 543 TCA GCC TCC CAA GTA GCT GGG ACC AAA GAC ATG CAC CAC TAC ACC TGG CTA ATT TTT ATT 602
 177  S   A   S   Q   V   A   G   T   K   D   M   H   H   Y   T   W   L   I   F   I  196
 603 TTT ATT TTT AAT TTT TTG AGA CAG AGT CTC AAC TCT GTC ACC CAG GCT GGA GTG CAG TGG 662
 197  F   I   F   N   F   L   R   Q   S   L   N  (S)  V   T   Q   A   G   V   Q   W  216
 663 CGC AAT CTT GGC TCA CTG CAA CCT CTG CCT CCC GGG TTC AAG TTA TTC TCC TGC CCC AGC 722
 217  R   N   L   G   S   L   Q   P   L   P   P   G   F   K   L   F   S   C   P  (S) 236
 723 CTC CTG AGT AGC TGG GAC TAC AGG CGC CCA CCA CGC CTA GCT AAT TTT TTT GTA TTT TTA 782
 237  L   L   S   S   W   D   Y   R   R   P   P   R   L   A   N   F   F   V   F   L  256
 783 GTA GAG ATG GGG TTC ACC ATG TTC GCC AGG TTG ATC TTG ATC TCT GGA CCT TGT GAT CTG 842
 257  V   E   M   G   F   T   M   F   A   R   L   I   L   I   S   G   P   C   D   L  276
 843 CCT GCC TCG GCC TCC CAA AGT GCT GGG ATT ACA GGC GTG AGC CAC CAC GCC CGG CTT ATT 902
 277  P   A  (S)  A   S   Q   S   A   G   I   T   G   V   S   H   H   A   R   L   I  296
 903 TTT AAT TTT TGT TTG TTT GAA ATG GAA TCT CAC TCT GTT ACC CAG GCT GGA GTG CAA TGG 962
 297  F   N   F   C   L   F   E   M   E   S   H   S   V   T   Q   A   G   V   Q   W  316
 963 CCA AAT CTC GGC TCA CTG CAA CCT CTG CCT CCC GGG CTC AAG CGA TTC TCC TGT CTC AGC 1022
 317  P   N   L   G   S   L   Q   P   L   P   P   G   L   K   R   F   S   C   L  (S) 336
1023 CTC CCA AGC AGC TGG GAT TAC GGG CAC CTG CCA CCA CAC CCC GCT AAT TTT TGT ATT TTC 1082
 337  L   P   S   S   W   D   Y   G   H   L   P   P   H   P   A   N   F   C   I   F  356
1083 ATT AGA GGC GGG GTT TCA CCA TAT TTG TCA GGC TGG TCT CAA ACT CCT GAC CTC AGG tgac 1143
 357  I   R   G   G   V  (S)  P   Y   L   S   G   W   S   Q  (T)  P   D   L   R       375
```

1144 ccacctgcctcagccttccaaagtgctgggattacaggcgtgagccacctcacccagccggctaatttagataaaaaaat 1223

1224 atgtagcaatgggggtcttgctatgttgcccaggctggtctcaaacttctggcttcatgcaatccttccaaatgagcca 1303

1304 caacacccagccagtcacattttttaaacagttacatctttattttagtatactagaaagtaatacaataaacatgtcaa 1383

1384 acctgcaaattcagtagtaacagagttctttttataacttttaaacaaagctttagagca 1442

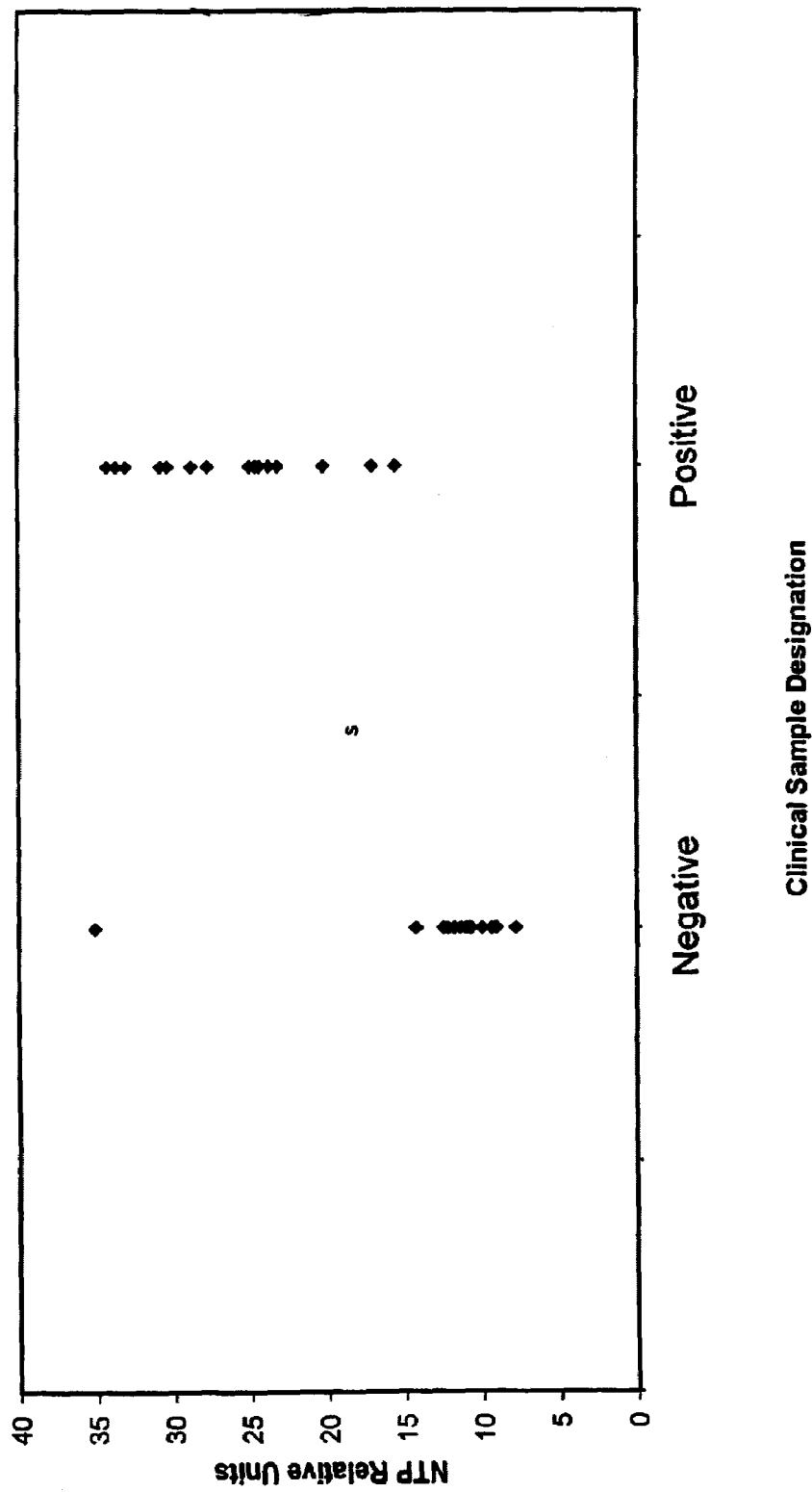
Figure 6: Competitive Affinity Assay in ELISA Format Using a HarIII Peptide - Antibody Conjugate

SEQUENCE LISTING

```
<160> NUMBER OF SEQ ID NOS: 12

<210> SEQ ID NO 1
<211> LENGTH: 1442
<212> TYPE: DNA
<213> ORGANISM: Unknown Organism
<220> FEATURE:
<221> NAME/KEY: CDS
<222> LOCATION: (15)..(1139)
<220> FEATURE:
<223> OTHER INFORMATION: Description of Unknown Organism: NTP DNA
      sequence

<400> SEQUENCE: 1
tttttttttt tgag atg gag ttt tcg ctc ttg ttg ccc agg ctg gag tgc       50
          Met Glu Phe Ser Leu Leu Leu Pro Arg Leu Glu Cys
            1               5                  10 aat ggc gca atc tca gct cac cgc aac ctc cgc ctc ccg ggt tca agc       98
Asn Gly Ala Ile Ser Ala His Arg Asn Leu Arg Leu Pro Gly Ser Ser
         15                  20                  25 gat tct cct gcc tca gcc tcc cca gta gct ggg att aca ggc atg tgc      146
Asp Ser Pro Ala Ser Ala Ser Pro Val Ala Gly Ile Thr Gly Met Cys
 30                  35                  40 acc cac gct cgg cta att ttg tat ttt ttt tta gta gag atg gag ttt      194
Thr His Ala Arg Leu Ile Leu Tyr Phe Phe Leu Val Glu Met Glu Phe
 45                  50                  55                  60 ctc cat gtt ggt cag gct ggt ctc gaa ctc ccg acc tca gat gat ccc      242
Leu His Val Gly Gln Ala Gly Leu Glu Leu Pro Thr Ser Asp Asp Pro
                 65                  70                  75 tcc gtc tcg gcc tcc caa agt gct aga tac agg act ggc cac cat gcc      290
Ser Val Ser Ala Ser Gln Ser Ala Arg Tyr Arg Thr Gly His His Ala
                 80                  85                  90 cgg ctc tgc ctg gct aat ttt tgt ggt aga aac agg gtt tca ctg atg      338
Arg Leu Cys Leu Ala Asn Phe Cys Gly Arg Asn Arg Val Ser Leu Met
         95                  100                 105 tgc cca agc tgg tct cct gag ctc aag cag tcc acc tgc ctc agc ctc      386
```

|     |     |     |     |     |     |     |     |     |     |     |     |     |     |
| --- | --- | --- | --- | --- | --- | --- | --- | --- | --- | --- | --- | --- | --- |
| Cys | Pro | Ser | Trp | Ser | Pro | Glu | Leu | Lys | Gln | Ser | Thr | Cys | Leu | Ser | Leu |
|     | 110 |     |     |     | 115 |     |     |     |     | 120 |     |     |     |

```
cca aag tgc tgg gat tac agg cgt gca gcc gtg cct ggc ctt ttt att     434
Pro Lys Cys Trp Asp Tyr Arg Arg Ala Ala Val Pro Gly Leu Phe Ile
125             130                 135                 140 tta ttt ttt tta aga cac agg tgt ccc act ctt acc cag gat gaa gtg     482
Leu Phe Phe Leu Arg His Arg Cys Pro Thr Leu Thr Gln Asp Glu Val
                145                 150                 155 cag tgg tgt gat cac agc tca ctg cag cct tca act cct gag atc aag     530
Gln Trp Cys Asp His Ser Ser Leu Gln Pro Ser Thr Pro Glu Ile Lys
            160                 165                 170 cat cct cct gcc tca gcc tcc caa gta gct ggg acc aaa gac atg cac     578
His Pro Pro Ala Ser Ala Ser Gln Val Ala Gly Thr Lys Asp Met His
            175                 180                 185 cac tac acc tgg cta att ttt att ttt att ttt aat ttt ttg aga cag     626
His Tyr Thr Trp Leu Ile Phe Ile Phe Ile Phe Asn Phe Leu Arg Gln
        190                 195                 200 agt ctc aac tct gtc acc cag gct gga gtg cag tgg cgc aat ctt ggc     674
Ser Leu Asn Ser Val Thr Gln Ala Gly Val Gln Trp Arg Asn Leu Gly
205                 210                 215                 220 tca ctg caa cct ctg cct ccc ggg ttc aag tta ttc tcc tgc ccc agc     722
Ser Leu Gln Pro Leu Pro Pro Gly Phe Lys Leu Phe Ser Cys Pro Ser
                225                 230                 235 ctc ctg agt agc tgg gac tac agg cgc cca cca cgc cta gct aat ttt     770
Leu Leu Ser Ser Trp Asp Tyr Arg Arg Pro Pro Arg Leu Ala Asn Phe
            240                 245                 250 ttt gta ttt tta gta gag atg ggg ttc acc atg ttc gcc agg ttg atc     818
Phe Val Phe Leu Val Glu Met Gly Phe Thr Met Phe Ala Arg Leu Ile
            255                 260                 265 ttg atc tct gga cct tgt gat ctg cct gcc tcg gcc tcc caa agt gct     866
Leu Ile Ser Gly Pro Cys Asp Leu Pro Ala Ser Ala Ser Gln Ser Ala
270                 275                 280 ggg att aca ggc gtg agc cac cac gcc cgg ctt att ttt aat ttt tgt     914
Gly Ile Thr Gly Val Ser His His Ala Arg Leu Ile Phe Asn Phe Cys
285                 290                 295                 300 ttg ttt gaa atg gaa tct cac tct gtt acc cag gct gga gtg caa tgg     962
Leu Phe Glu Met Glu Ser His Ser Val Thr Gln Ala Gly Val Gln Trp
                305                 310                 315 cca aat ctc ggc tca ctg caa cct ctg cct ccc ggg ctc aag cga ttc    1010
Pro Asn Leu Gly Ser Leu Gln Pro Leu Pro Pro Gly Leu Lys Arg Phe
            320                 325                 330 tcc tgt ctc agc ctc cca agc agc tgg gat tac ggg cac ctg cca cca    1058
Ser Cys Leu Ser Leu Pro Ser Ser Trp Asp Tyr Gly His Leu Pro Pro
            335                 340                 345 cac ccc gct aat ttt tgt att ttc att aga ggc ggg gtt tca cca tat    1106
His Pro Ala Asn Phe Cys Ile Phe Ile Arg Gly Gly Val Ser Pro Tyr
350                 355                 360 ttg tca ggc tgg tct caa act cct gac ctc agg tgacccacct gcctcagcct  1159
Leu Ser Gly Trp Ser Gln Thr Pro Asp Leu Arg
365                 370                 375 tccaaagtgc tgggattaca ggcgtgagcc acctcaccca gccggctaat ttagataaaa  1219
aaatatgtag caatgggggg tcttgctatg ttgcccaggc tggtctcaaa cttctggctt  1279
catgcaatcc ttccaaatga gccacaacac ccagccagtc acatttttta aacagttaca  1339
tctttatttt agtatactag aaagtaatac aataaacatg tcaaacctgc aaattcagta  1399
gtaacagagt tcttttataa cttttaaaca aagctttaga gca                    1442

<210> SEQ ID NO 2
```

```
<211> LENGTH: 375
<212> TYPE: PRT
<213> ORGANISM: Unknown Organism
<220> FEATURE:
<223> OTHER INFORMATION: Description of Unknown Organism: NTP amino acid
      sequence

<400> SEQUENCE: 2

Met Glu Phe Ser Leu Leu Pro Arg Leu Glu Cys Asn Gly Ala Ile
 1               5                  10                  15

Ser Ala His Arg Asn Leu Arg Leu Pro Gly Ser Ser Asp Ser Pro Ala
                20                  25                  30

Ser Ala Ser Pro Val Ala Gly Ile Thr Gly Met Cys Thr His Ala Arg
                35                  40                  45

Leu Ile Leu Tyr Phe Phe Leu Val Glu Met Glu Phe Leu His Val Gly
            50                  55                  60

Gln Ala Gly Leu Glu Leu Pro Thr Ser Asp Asp Pro Ser Val Ser Ala
 65                  70                  75                  80

Ser Gln Ser Ala Arg Tyr Arg Thr Gly His His Ala Arg Leu Cys Leu
                85                  90                  95

Ala Asn Phe Cys Gly Arg Asn Arg Val Ser Leu Met Cys Pro Ser Trp
                100                 105                 110

Ser Pro Glu Leu Lys Gln Ser Thr Cys Leu Ser Leu Pro Lys Cys Trp
                115                 120                 125

Asp Tyr Arg Arg Ala Ala Val Pro Gly Leu Phe Ile Leu Phe Phe Leu
                130                 135                 140

Arg His Arg Cys Pro Thr Leu Thr Gln Asp Glu Val Gln Trp Cys Asp
145                 150                 155                 160

His Ser Ser Leu Gln Pro Ser Thr Pro Glu Ile Lys His Pro Pro Ala
                165                 170                 175

Ser Ala Ser Gln Val Ala Gly Thr Lys Asp Met His His Tyr Thr Trp
                180                 185                 190

Leu Ile Phe Ile Phe Ile Phe Asn Phe Leu Arg Gln Ser Leu Asn Ser
                195                 200                 205

Val Thr Gln Ala Gly Val Gln Trp Arg Asn Leu Gly Ser Leu Gln Pro
                210                 215                 220

Leu Pro Pro Gly Phe Lys Leu Phe Ser Cys Pro Ser Leu Leu Ser Ser
225                 230                 235                 240

Trp Asp Tyr Arg Arg Pro Pro Arg Leu Ala Asn Phe Val Phe Leu
                245                 250                 255

Val Glu Met Gly Phe Thr Met Phe Ala Arg Leu Ile Leu Ile Ser Gly
                260                 265                 270

Pro Cys Asp Leu Pro Ala Ser Ala Ser Gln Ser Ala Gly Ile Thr Gly
                275                 280                 285

Val Ser His His Ala Arg Leu Ile Phe Asn Phe Cys Leu Phe Glu Met
                290                 295                 300

Glu Ser His Ser Val Thr Gln Ala Gly Val Gln Trp Pro Asn Leu Gly
305                 310                 315                 320

Ser Leu Gln Pro Leu Pro Pro Gly Leu Lys Arg Phe Ser Cys Leu Ser
                325                 330                 335

Leu Pro Ser Ser Trp Asp Tyr Gly His Leu Pro Pro His Pro Ala Asn
                340                 345                 350

Phe Cys Ile Phe Ile Arg Gly Gly Val Ser Pro Tyr Leu Ser Gly Trp
                355                 360                 365

Ser Gln Thr Pro Asp Leu Arg
```

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ala Arg Leu Met Leu
 1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      NTP-1 peptide

<400> SEQUENCE: 4

Leu His Ala Arg Leu Cys Leu Ala Asn Phe Cys Gly Arg Asn Arg Val
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      NTP-2 peptide

<400> SEQUENCE: 5

Leu Ala Arg Leu Cys Leu Ala Asn Phe Cys Gly Asn Asn Asn Val
 1               5                  10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      NTP-3 peptide

<400> SEQUENCE: 6

Cys Ala Arg Tyr Arg Thr Gly His His Ala Arg Leu Met
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      NTP-4 peptide

<400> SEQUENCE: 7

His His Ala Arg Leu Pro Leu Ala Asn Phe Cys Gly
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued

```
      NTP-5 peptide

<400> SEQUENCE: 8

Arg Thr Gly His His Ala Arg Leu Cys Leu Ala Asn Phe Cys
 1               5                  10

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      NTP-6 peptide

<400> SEQUENCE: 9

Cys Glu Ser Ala Arg Tyr Arg Thr Gly His His Ala Arg Leu Cys
 1               5                  10                  15

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      NTP-7 peptide

<400> SEQUENCE: 10

Asp Asn Thr His His Ala Arg Leu Ile Leu
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      NTP-8 peptide

<400> SEQUENCE: 11

Ser His His Ala Arg Leu Ile Leu
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Arg Cys Leu
 1
```

PREFERRED SEGMENTS OF NEURAL THREAD PROTEIN

FIELD OF THE INVENTION

The present invention is directed to preferred segments of neural thread protein useful in, for example, binding assays, protein and antibody purification, therapeutics, and diagnostics.

BACKGROUND OF THE INVENTION

Alzheimer's disease (AD) is a presently incurable neurodegenerative disease affecting at least 12 million people worldwide. AD is predominantly a disease of the elderly, with a rate of incidence of about 1% of those aged 65 and rising to an estimated 40% by age 85. As the population as a whole grows older, because of medical advances, increasing life expectancies, and aging of the baby boomer generation, the overall incidence of AD is expected to rise and present even more of a burden to heath care systems and to patients and their caregivers and family.

No effective treatment of AD exists today. Currently available treatments such as Aricept® (donepezil HCl; Pfizer Corp.), Exelon® (rivastigmine tartrate; Novartis Pharmaceuticals Corp.) and Cognex® (tacrine; Warner Lambert Corp.) are intended to provide a measure of symptomatic relief for patients with mild to moderate AD and do not address the causes of the disease.

Clinical diagnosis of AD is also imperfect; accuracy varies from roughly 50-60% for general practitioners to 80-90% for Alzheimer's disease specialists at referral centers (Molsa et al., *J. Neurol. Neurosurg. Psychiatry*, 48(11):1085-90 (1985); Rocca et al., *Ann. Neurol.*, 19:415-424 (1986); Burns et al., *BMJ*, 301(6759):1026 (1990); Risse et al., *Am. J. Psychiatry*, 147(2):168-72 (1990); Gilleard et al., *Acta Psychiatr. Scand.*, 85(4):264-9 (1992); Mendez et al., *Alzheimer Dis. Assoc. Disord.*, 6:35-43 (1992); Fleming et al., *Mayo Clin. Proc.*, 7:1093-1107 (1995); Corey-Bloom et al., *Neurology*, 45:211-218 (1995); and Bowler et al., *J. Neurol. Neurosurg. Psychiatry*, 64(1):18-24 (1998). There is an average delay of nearly three years from initial symptoms to when the diagnosis of AD is made (Jorst et al., *J. Am. Geriatr. Soc.*, 43(11):1248-55 (1995)).

It has been recognized that a reliable biomarker would be of significant help in the accurate and early diagnosis of AD (Growdon et al., *Neurobiol. Aging*, 19:109-116 (1998)). Although several biochemical and genetic markers are currently available, their clinico-pathologic correlations are generally considered too low for routine clinical use. For example, apolipoprotein E ϵ4 allele is a genetic risk factor which is found only in 50% of AD cases (Myers et al., *Neurology*, 46(3):673-7 (1996)), and tau and β-amyloid protein measurements in cerebrospinal fluid (CSF) and serum Aβ have significant overlap between AD and non-AD levels, limiting their usefulness (Pirttila et al., *J. Neurol. Sci.*, 127(1):90-5 (1994); Arai et al., *Ann. Neurol.*, 38:649-652 (1995); Jensen et al., *Neurosci. Lett.*, 186(2-3):189-91 (1995); Motter et al., *Ann. Neurol.*, 38(4):643-8 (1995); Munroe et al., *Ann. Clin. Lab. Sci.*, 25(3):207-17 (1995); Tata et al., *J. Neurol. Neurosurg. Psychiatr.*, 59:280-283 (1995); Vigo-Pelfrey et al., *Neurology*, 45(4):788-93 (1995); Iwatsubo T., *Neurobiol. Aging*, 19:161-163 (1998); Nitsch et al., *Ann. Neurol.*, 37(4):512-8 (1995); van Gool et al., *Ann. Neurol.*, 37(2):277-9 (1995); Tamaoka et al., *J. Neurol. Sci.*, 151(1-2):65-8 (1996); and Pirtilla et al., *Arch. Neurol.*, 53(2):189-93 (1996)). Other proposed markers, such as pupillary response to tropicamide (Scinto et al., *Science*, 266:1051-1054 (1994); and Growdon et al., *Arch. Neurol.*, 54(7):841-4 (1997)) and serum factors such as p-97 (Kennard et al., *Nat. Med.*, 2(11):1230-5 (1996)), have not yet been validated in repeated controlled clinical studies. The major drawbacks of most proposed AD markers are that they are usually not brain-specific molecules associated with AD pathology and that they are not reliably measurable in peripheral fluids.

Neural thread proteins (NTP) are a novel family of recently characterized brain proteins. NTP is a ~41 kD membrane associated phosphoprotein with functions related to neuritic sprouting and cell death (de la Monte et al., *J. Clin. Invest.*, 100:3093-3104 (1997); and de la Monte et al., *Alz. Rep.*, 2:327-332 (1999)). There is compelling evidence linking NTP with AD. NTP mRNA is upregulated in AD brain compared to controls; NTP protein levels in brain and in CSF are higher in AD than controls; and NTP immunoreactivity is clearly found in senile plaques, in neurofibrillary tangles (NFT), in degenerating neurons, neuropil threads, and dystrophic neuritic sprouts in AD and Down syndrome brains (Ozturk et al., *Proc. Natl. Acad. Sci. USA*, 86:419-423 (1989); de la Monte et al., *J. Clin. Invest.*, 86(3):1004-13 (1990); de la Monte et al., *J. Neurol. Sci.*, 113(2):152-64 (1992); de la Monte et al., *Ann. Neurol.*, 32(6):733-42 (1992); de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2):118-25 (1996); de la Monte et al., *J. Clin. Invest.*, 100:3093-3104 (1997); and de la Monte et al., *Alz. Rep.*, 2:327-332 (1999)). NTP accumulation in neurons occurs early in AD neurodegeneration (before NFT formation). NTP has also been identified Down's Syndrome brain tissue (Wands et al., International Patent Publication No. WO 90/06993; de la Monte et al., *Alz. Rep.*, 2:327-332 (1999)). Most patients with Down's Syndrome exhibit neuropathology similar to that of AD after middle age and develop many cognitive defects similar to those of AD later in life.

NTP levels in the cerebrospinal fluid (CSF) of AD patients and controls were shown to be consistently elevated in AD (Chong et al., *J. Clin. Lab. Anal.*, 6(6):379-83 (1992); de la Monte et al., *Ann. Neurol.*, 32:733-742 (1992); de la Monte et al., *J. Clin. Invest.*, 100:3093-3104 (1997); Ghanbari et al., *J. Clin. Lab. Anal.*, 12(4):223-6 (1998); Ghanbari et al., *J. Contemp. Neurol.*, 1998:2-8 (1998); Kahle et al., *Neurology*, 54(7):1498-504 (2000)). Specificity of NTP elevation in AD was shown in comparison to non-AD neurological disease controls, and NTP elevation was positively correlated with degree of dementia (de la Monte et al., *J. Clin. Invest.*, 100:3093-3104 (1997); and de la Monte et al., *Alz. Rep.*, 2:327-332 (1999); and Kahle et al., *Neurology*, 54(7): 1498-504 (2000)). In one major study, 89% of patients with early AD had NTP levels of above 2 ng/mL of CSF and 89% of non-AD controls below 2 ng/mL of CSF (de la Monte et al., *J. Clin. Invest.*, 100:3093-3104 (1997)).

Subsequently, the NTP protein was identified in urine by high performance liquid chromatography, capillary electrophoresis, and ELISA (Ghanbari et al., *J. Clin. Lab. Anal.*, 12(4):285-288 (1998); and de la Monte et al., *Alz. Rep.*, 2:327-332 (1999)). Urinary NTP levels were found to correlate with CSF levels in AD patients and controls and to be significantly elevated in AD patients as compared to non-AD patients (Ghanbari et al., *J. Clin. Lab. Anal.*, 12(4):285-288 (1998)). An assay using gold particles with bound monoclonal anti-NTP in the liquid phase was developed for urine samples and demonstrated to be both highly sensitive and specific for AD (Fitzpatrick et al., *Alzheimer's Reports*, 3(3):155-159 (2000)).

There is a need to improve upon the existing assays for NTP, including a need to develop point-of-care assays for NTP which can be conducted in a general medical laboratory or a doctor's office. Technical advances such as methods to routinely purify native NTP from urine in a cost-effective manner or the development of easily manufactured analogs to NTP would also improve any such assays There is evidence showing that NTP may play a direct role in the pathogenesis of AD, thereby making it a target for drug development for the treatment of AD. NTP is associated with neuritic sprouting; abnormal neuritic sprouting is associated with AD. Over-expression of NTP can cause cellular accumulations of phospho-tau, which in turn precedes the formation of NFT, an important neuroanatomical correlate of dementia in AD (de la Monte et al., *Alz. Rep.*, 2:327-332 (1999)). In addition, over-expression of NTP can cause increased cell death of an apoptotic nature linked to oxidative stress (de la Monte et al., 1999). Inhibiting the expression or the biochemical action of NTP offers one promising route to an effective treatment for AD.

The gene and predicted protein sequence for NTP has been identified and described (de la Monte et al., *J. Clin. Invest.*, 100:3093-3104 (1997)). Neural thread protein was first described and claimed in U.S. Pat. Nos. 5,948,634; 5,948,888; and 5,830,670, all for "Neural Thread Protein Gene Expression and Detection of Alzheimer's Disease."

Other species of neural thread protein (~26 kD, ~21 kD, ~17 kD and ~15 kD) have been identified and associated with neuroectodermal tumors, astrocytomas, and glioblastomas and with injury due to hypoxia, ischemia, or cerebral infarction (de la Monte et al., *J. Neuropathol. Exp. Neurol.*, 55(10):1038-50 (1996), de la Monte et al., *J. Neurol. Sci.*, 138(1-2):26-35 (1996); de la Monte et al., *J. Neurol. Sci.*, 135(2):118-25 (1996); de la Monte et al., *J. Clin. Invest.*, 100:3093-3104 (1997); and de la Monte et al., *Alz. Rep.*, 2:327-332 (1999)).

There is a need in the art for improved NTP compositions, useful in therapeutics and diagnostics related to AD and Down's Syndrome, and for compositions relating to the other species of neural thread protein useful in threapeutics and diagnostics for neuroectodermal tumors, astrocytomas, glioblastomas, and other neurodegenerative disorders and for injury due to hypoxia, ischemia and cerebral infarction. The present invention satisfies these needs.

SUMMARY OF THE INVENTION

The present invention is directed to a family of novel repeat sequences of NTP having the consensus sequence of "H A R L I L (portion of SEQ ID NO: 2, residues 46-51)" and homologs thereof. Harlil peptides encompassed by the invention include, but are not limited to, "H A R L I L (portion of SEQ ID NO: 2, residues 46-51)," "H A R L C L (portion of SEQ ID NO: 2, residues 91-96)," "H H A R L C L (portion of SEQ ID NO: 2, residues 90-96)," "H A R L (portion of SEQ ID NO: 2, residues 91-94)," "M F A R L I L (portion of SEQ ID NO: 2, residues 263-269)," "A R L I L (portion of SEQ ID NO: 2, residues 265-269)," "H A R L I F (portion of SEQ ID NO: 2, residues 292-297)," "H H A R L I F (portion of SEQ ID NO: 2, residues 291-297)," and homologs and binding partners thereof. This group of NTP peptides, and homologous peptides, are collectively referred to as "Harlil peptides."

The invention arises from the unexpected discovery that the Harlil peptides have unique binding characteristics:

they have an affinity to bind to NTP, thereby making them useful for purification of NTP from bodily fluids, such as urine, CSF, or blood, as a binding partner for capture of NTP, for the detection and measurement of NTP in bodily fluids, such as urine, CSF, or blood, for drug development for AD and Down's syndrome, as well as other matters disclosed below;

they have an affinity to bind to many immunoglobulins, thereby making them useful for the purification of immunoglobulins, the detection and measurement of such immunoglobulins;

they have an affinity to bind to themselves, thereby making them useful for the separation, assay measurement, and/or purification of proteins conjugated to them, the use as an NTP analog in an assay, as well as other matters disclosed below; and they appear to function in self-assembly and/or interaction with NTP with other proteins making them useful as therapeutic targets.

The invention also encompasses antibodies directed to the Harlil peptide sequences and functional fragments of such antibodies. The antibodies can be monoclonal or polyclonal antibodies.

Yet another aspect of the invention is directed to binding partners of the Harlil sequences on the NTP protein. Such binding partners include, but are not limited to, homologous peptides, organic peptide mimetics, antibodies or portions of antibodies, and paralogues.

The invention encompasses nucleic acids corresponding to the Harlil peptides, vectors containing at least one nucleic acid encoding at least one Harlil peptide, and host cells for propagating such vectors, such as *E. coli* or other useful bacteria or yeast species. The vectors can be used, for example, in therapeutic treatments or in methods of making Harlil peptides.

This invention further discloses methods of making Harlil peptides, antibodies, and nucleic acids of the invention using conventional techniques known in the art.

Another aspect of the invention is directed to pharmaceutical compositions comprising one or more Harlil peptides, Harlil peptide mimetics, and/or binding partners thereto, and pharmaceutical compositions comprising one or more nucleic acids encoding one or more Harlil peptides. The pharmaceutical compositions may be useful, for example, in therapeutic treatments for AD, neuroectodermal tumors, astrocytomas, glioblastomas, and other neurodegenerative disorders.

The invention encompasses the use of a Harlil peptide, corresponding nucleic acid, or Harlil mimetic in diagnostics for AD, neuroectodermal tumors, astrocytomas, glioblastomas, and other neurodegenerative disorders. Diagnostic tests employing one or more Harlil peptides may be useful for testing for the presence of antibodies to NTP or to Harlil peptide sequences, which are indicative of the presence of NTP. While NTP is found in all humans, there is an elevated amount found in patients medically diagnosed as having AD (i.e., DSM4 patients). Alternatively, a diagnostic test can employ one or more antibodies to one or more Harlil peptide sequences, which are useful in detecting the presence of NTP. The quantity of NTP correlates with the presence of AD, neuroectdermal tumors, astrocytomas, glioblastomas, other neurodegenerative disorders. Finally, a diagnostic test can employ one or more nucleic acids encoding one or more Harlil peptides. Hybridization between such nucleic acids and nucleic acids in a biological sample is indicative of the presence of NTP. Again, the quantity of NTP correlates with the presence of AD, neuroectodermal tumors, astrocytomas, glioblastomas, and other neurodegenerative disorders. The Harlil peptides, Harlil mimetics, antibodies, and nucleic acids of the invention can be labeled in such diagnostic tests.

Yet another aspect of the present invention is directed to diagnostic test kits for implementing a diagnostic method of the invention. Such test kits comprise one or more Harlil peptides, Harlil mimetics, antibodies, Harlil binding partners, and/or nucleic acids, and suitable reagents.

The invention also encompasses methods of purifying NTP from solutions using a Harlil peptide or Harlil mimetic. Kits for applying such methods are encompassed by the invention. Such a kit comprises at least one Harlil peptide, Harlil mimetic, or mixtures thereof and suitable reagents.

Also encompassed by the invention are methods and kits for purifying antibodies using a Harlil peptide of the invention. Such a kit comprises a Harlil peptide of the invention and suitable reagents.

The present invention is further directed to a method of treatment for AD, neuroectodermal tumors, astrocytomas, glioblastomas, or other neurodegenerative disorder comprising administering to a mammal in need a therapeutically effective amount of one or more Harlil peptides, Harlil mimetics (not limited to Harlil peptide mimetics), antibodies, and/or nucleic acids of the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows the complete NTP sequence (SEQ ID NOS 1 & 2) and the location of the Harlil sequences within the complete NTP sequence (de la Monte et al., *J. Neuropathol. Exp. Neurol.*, 55:1038-1050 (1996));

FIG. 6: Shows the results of a competitive affinity assay to distinguish AD diagnosed samples for age-matched normals in an ELISA format using a Harlil peptide, which demonstrates a threshold amount present in AD-positive patients (data described in Example 8).

DETAILED DESCRIPTION OF THE INVENTION

Figure 2:
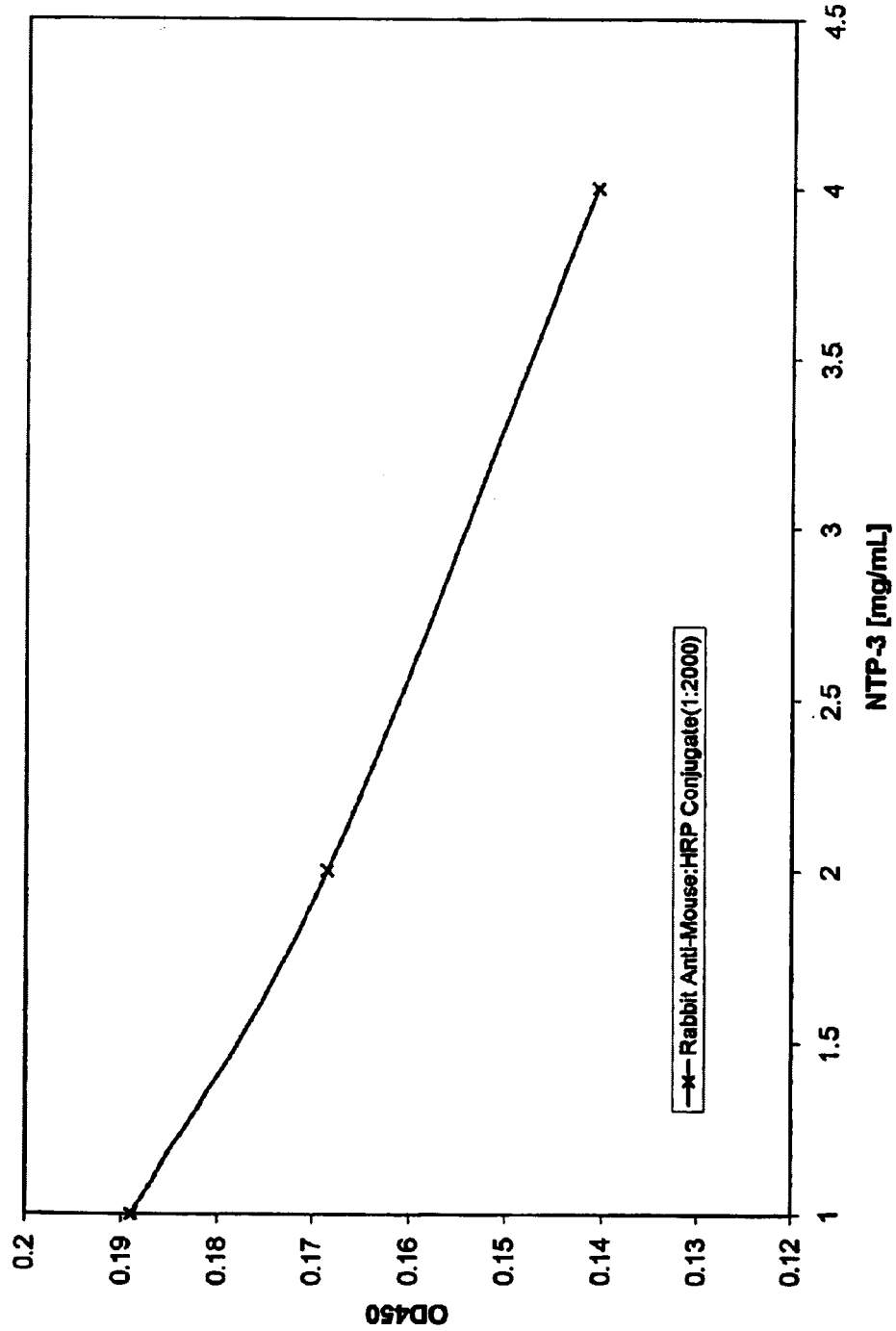
FIG. 2: Shows the inhibition of rabbit anti-mouse immunoglobulin conjugate binding to a Harlil peptide (NTP-3) coated microtiter plate as a function of competing NTP-3/RGG concentration (x axis) (data described in Example 5)

The present invention is directed to a composition comprising a novel repeat sequence of NTP, referred to as "the Harlil sequence." The sequence occurs four times in the amino acid sequence of NTP:

(a) 45-51 T H A R L I L (portion of SEQ ID NO: 2)
(b) 90-96 H H A R L C L (portion of SEQ ID NO: 2)
(c) 263-269 M F A R L I L (portion of SEQ ID NO: 2)
(d) 292-296 H H A R L I F (portion of SEQ ID NO: 2) See FIG. 1.

The invention encompasses peptides having the sequence of any of regions (a), (b), (c), (d), or homologs of these (including but not limited to "H A R L M L")(SEQ ID NO: 3). The Harlil peptides can also have additional amino acid residues before or after the Harlil sequence on linker peptides. The additional amino acid residues or linker peptides may be those found in the NTP sequence before and after the Harlil sequence. For example, the amino acid residues G I T G M C T (portion of SEQ ID NO: 2, residues 39-45) occur before residue 46 and the amino acid residues Y F F L V (portion of SEQ ID NO: 2, residues 52-56) occur after amino acid 50 in the NTP sequence. Thus, a Harlil peptide encompassed by the invention includes the NTP peptide G I T G M C T H A R L I L Y F F L V (portion of SEQ ID NO: 2, residues 50-56). For the Harlil peptides recited in (b), (c), and (d), the additional amino acid residues are those that flank the Harlil sequence in the NTP sequence. However, there is no evidence that the flanking sequences serve as other than a linker. Preferably, the Harlil peptide having additional amino acid residues does not exceed 25 total amino acid residues in length.

Homologs and variants of the Harlil peptides are also encompassed by the scope of the invention. It is common to vary peptide sequences by substituting one amino acid for another. Depending on the purpose for which the amino acid is being varied, the amino acid can be replaced with a similar or homologous amino acid or a dissimilar amino acid. There are many scales on which amino acids can be ranked as similar or homologous. (Gunnar von Heijne, *Sequence Analysis in Molecular Biology*, p. 123-39 (Academic Press, New York, N.Y. 1987).

The Harlil repeat sequence has the following unique characteristics: (1) it can bind to NTP; (2) it can bind to many immunoglobulins; and (3) it can bind to itself. These unique characteristics enable and suggest various diagnostic and therapeutic applications, as described below.

A. Compositions

The present invention is directed to Harlil peptides of NTP, the use of such peptides, peptide mimetics, binding partners, and/or homologs as affinity binding partners of NTP for assay or purification of NTP, the use of Harlil peptides, peptide mimetics, and homologs thereof to block the Harlil peptide sites on NTP, or the use of substances that interact with NTP through the Harlil sequences. Also encompassed by the invention are antibodies directed to such Harlil peptide sequences, and nucleic acids corresponding to the Harlil peptides and homologs thereof.

Harlil peptides and homologs thereof can be made using conventional peptide synthesis techniques. Mimetics of Harlil peptides can be developed using combinatorial chemistry techniques.

Monoclonal antibodies to a Harlil peptide sequence can be made, for example, by the hybridoma method first described by Kohler & Milstein, *Nature*, 256:495 (1975), or by recombinant DNA methods (see e.g., U.S. Pat. No. 4,816,567). Polyclonal antibodies (i.e., antisera), can be made, for example, by immunizing host animals such as rabbits or sheep, with a Harlil peptide as an immunogen. The immunization typically involves repeated inoculations with the immunogen, typically at least two at about one week intervals. Such inoculation raises an immune response against the immunogen and causes the inoculated host's immune system to produce antibodies against the immunogen. Serum from the immunized host will usually be collected about three to ten days after the final booster. Immunoglobulins may be separated from the serum by ammonium sulfate precipitation, gel electrophoresis, dialysis, chromatography, or other conventional separation and purification techniques.

Nucleic acids corresponding to Harlil peptides can be made, for example, using (a) standard recombinant methods, (b) synthetic techniques, or (c) combinations thereof.

B. Properties of the Harlil Peptides

1. Binding to NTP

The Harlil sequence shows binding specificity to NTP. When a Harlil peptide, or an analogue thereof, is immobilized it can be used to purify NTP from solutions. When it is used to capture NTP as part of an affinity assay, the binding to NTP is very specific and is unaffected by pH from 3.5 through pH 8. The sensitivity of this affinity assay is at least as high as an immunoassay. For example, a positive urine pool which contains about 0.5 ng/mL NTP by ELISA can be diluted almost 4 fold and still be differentiated from a negative pool by this affinity assay (this is described in more detail in Example 6, below). Moreover, assay sensitivity can be improved by using a more sensitive detection means, such as by using fluorescent or chemoluminescent substrates or radio-labeled assays.

Because the Harlil peptides of the invention bind specifically to NTP, they can be used in diagnostic assays for detecting the presence of NTP or antibodies to NTP in a biological sample. Above normal levels of NTP in bodily fluids have been shown to indicate the presence of AD, Down's Syndrome, or other degenerative brain disease.

2. Binding to Immunoglobulins

Harlil peptides bind to many immunoglobulins. The peptide binding appears to be via the Fc portion of the antibody, and not via the Fab portion. The binding to immunoglobulins occurs at physiological pH, though some immunoglobulins also bind at lower pH's. Binding at a lower pH indicates the strong affinity between the Harlil peptide and certain antibodies, and eliminates the possibility that the binding was due to charge/charge interactions rather than affinity.

Because Harlil peptides bind to immunoglobulins, they are useful in the purification of immunoglobulin molecules. The Harlil monomer affinity for immunoglobulin is quite low and thus, the avidity of Harlil conjugates can be controlled by controlling peptide density. With increased Harlil peptide density, the affinity for immunoglobulin increases. It is desirable to use low to moderate affinity columns because high affinity columns require harsh elution conditions, which can denature proteins and antibodies, and elute in broad dilute peaks, which is undesirable because of dilution of eluted products (Wikström et al., *J. of Chromatography*, 597:83-92 (1992)). Such dilution requires further concentration of the eluted proteins or antibodies, and results in loss and/or damage of protein or antibody product.

In contrast, low affinity chromatography, such as that which can be used with a Harlil peptide, has the advantage of sharpening the elution peak and avoiding harsh conditions. Ibid. Such purification procedures are valuable for purifying therapeutic and diagnostic antibodies by providing purified proteins useful in pharmaceutical and diagnostic applications.

Prior known peptide analogs useful for immunoglobulin purification have much longer sequences than that of a Harlil peptide and appear to require or mimic a secondary structure through which they interact with immunoglobulins (Fassina et al., *J. of Mol. Recognition*, 9:564-569 (1996); Guerrier et al., *J. of Mol. Recognition*, 11:107-109 (1998); Palombo et al., *J. of Mol. Recognition*, 11:247-249 (1998); Braisted et al., *Proc. Natl. Acad. Sci. USA*, 93:5688-5692 (1996); Fassina et al., *J. of Mol. Recognition*, 11:128-133 (1998); Palombo et al., *J. of Mol. Recognition*, 11:243-246 (1998); Li et al., *Nat. Biotechnol.*, 16:190-195 (1998); and U.S. Pat. Nos. 5,084,559; 5,100,788; 6,013,763. The relatively short Harlil peptides of the invention are much easier and cost effective to produce and store.

Yet another application of the Harlil peptides of the invention relates to their use in diagnostic tests in formats such as ELISA and immunochromatography strips. Because the Harlil peptides of the invention bind to immunoglobulins, the peptides provide a cost-effective trap material substitute for anti-antibody and Proteins A and G for capture, separation, or anchorage in immunoassay systems. The current trap materials employed in ELISA and immunochromatography strips, i.e., anti-antibody and Proteins A and G, are expensive to make and maintain. This is in contrast to the relatively simple to make and cost-effective to store Harlil peptides of the invention.

3. Binding to Itself

The Harlil peptides and analogues of the invention are capable of binding to themselves, and thus when conjugated to proteins, the proteins will self-aggregate if they are not maintained at a very low pH or at very low dilution. The carrier protein may self-aggregate and precipitate out of solution at neutral pH.

In addition, because of its unique self-binding characteristic, a Harlil peptide can be used as an NTP analog in an assay. This is because the Harlil peptides duplicate the self-binding characteristic of NTP. In a sequential or competitive assay, NTP will bind to the Harlil peptide conjugate solid phase, and remain on during washes where it blocks the binding of immunoglobulin (such as rabbit IgG). The Harlil peptides can also be used as a capture antibody replacement in a sandwich assay. The Harlil peptides of the invention are less expensive and more cost effective assay materials than the NTP protein.

The self-aggregation property of Harlil peptides may have therapeutic applications. Because Harlil sequences cause proteins to which they are conjugated to bind to one another, this indicates that through these sequences NTP self-associates and/or associates with other proteins. This association could be intramolecular or intermolecular. The ability of an affinity column and a microtiter plate to bind free NTP (as described in the examples, below) indicates that in native NTP the Harlil sequence is probably surface accessible.

It is possible that the toxicity of NTP is in whole or part due to the highly interactive Harlil sequences. Thus, toxicity of NTP could be due to self-aggregation or it could be due to interaction of the highly reactive Harlil sequences with other cerebral components. By blocking this sequence of NTP, one may block its interactive capability.

It is clear that NTP participates in the neurodegenerative cascade. The ability to interrupt or redirect the cascade by targeting NTP offers a therapeutic opportunity. For example, it may be possible to intervene therapeutically by using the ability of the Harlil peptides to interact with NTP binding sites, thus blocking potential reactive sites on NTP. Alternatively, the Harlil peptides and mimetics of the invention may be useful to target drugs to cells expressing the Harlil sequence.

Peptides that self associate have been used in biomaterials as bioadhesives. Thus one can use the self associative or self recognition qualities of the peptide to induce non-associative proteins or peptides to associate, to anchor moities to surfaces, or to direct molecules to targeted sites. It is recognized that such cell adhesion inducing peptides could be useful in the design of synthetic tissues and organs (Mayo, K. H., *TIBTECH,* 18:212-217 (May, 2000). Such materials have also shown themselves useful in construction of gel systems that are pH and binding sensitive (Id.). In addition, polymerization and/or multiple repeats of Harlil peptide sequences could provide compositions having structural features and higher avidity.

The repetition of the Harlil sequence in the NTP sequence indicates that the Harlil sequence probably plays a role in the assembly or polymerization of NTP. For example, in collagen the regions of the separate strands that self associate at sites that subsequently form pyridinoline linkages also exhibit high homology, indicating that these self-identifying homologous regions serve a key structural and functional purpose. It is likely that the "HARLIL" sites individually or in polymer array interact with other brain proteins and are key to the functionality of NTP.

If NTP overproduction contributes to AD and related disease neurodegenerative disease pathology, then the production or folding of the NTP protein might be inhibited, and/or the polymerization or the interaction of NTP with other components might be prevented, with therapeutics based on the HARLIL (portion of SEQ ID NO: 2, residues 46-51) model. For example, if by administration of one or more Harlil peptide or Harlil mimetics, NTP aggregation, or folding or assembly, could be inhibited, one might expect enhanced protease degradation of NTP: Thus one might accomplish removal of excess NTP by administration of one or more Harlil peptide or Harlil mimetics. Alternately a Harlil peptide or Harlil mimetic therapeutic may be useful to control the interaction of NTP monomer or aggregate with other components of the neurodegenerative cascade.

Numerous proteins that self assemble or polymerize have repeat structures. The best known is collagen that bears the short repeat sequence gly X Y as many a six times per chain. (Lacy et al., "Identification of FLRT1, FLRT2 and FLRT3: a novel family of transmembrane leucine rich repeat proteins," *Genomics,* 62(3):417-26 (1999).) Other studies have shown that specific repeating sequences are involved in nucleation of binding. (Snellman et al., "A short sequence in the N-terminal region is required for the trimerization of type XIII collagen and is conserved in other collagenous transmembrane proteins," *EMBO J.,* 19(19):5051-59 (2000).) Further there are studies showing that the collagen peptide Pro Pro Gly, which is critical to self assembly, is also critical in the interaction of procollagen with the chaperone HSP7. (Koide et al., Conformational requirements of collagenous peptides for recognition by the chaperone protein HSP47," *Biol. Chem.,* 275(36):27957-27963 (2000).) The specificity of self recognition in laminin has been studied. (Schittny, J. C., "Affinity Retardation Chromatography: Charaterization of the Method and Its Application," *Anal. Biochem.,* 222: 140-148 (1994).)

Thus, it is evident that proteins that polymerize or form fibrilar structures do so generally by self assembly through specific domains on the protein recognizing specific domains on self (self-recognition). Further, these proteins may use these same recognition sites for interactions with other proteins. As with Protein A interactions with Fc (Deisenhofer, J., "Crystallographic Refinement and Atomic Models of a Human Fc Fragment and Its complex with Fragment B of Protein A from *Staphylococcus aureus* at 2.9- and 2.8-A Resolution," *Biochem.,* 20(9):2361-2370 (1981)), these interactions like that of the Harlil sequence appear to be through hydrophobic and ionic interactions.

In the case of NTP it appears that the Harlil domains, which function most probably in self assembly, are highly homologous and, indeed, almost completely conserved. The "leucine zipper" uses self-recognition in which leucine rich stretches bind together. A leucine zipper is, however, not as unique as the Harlil sequence. The Harlil sequence is envisaged to play a critical role in self assembly and the interaction of NTP with other brain components.

Prions and experiments with prion elements. in yeast provide evidence that proteins can assume a self aggregating conformation. (Serio et al., "Nucleated Conformational Conversion and the Replication of Conformational Information by a Prion Determinant," *Science,* 289:1317-21 (2000); and Sparrer H. E., "Evidence for the Prion Hypothesis: Induction of the Yeast (PSI+) Factor by in vitro-Converted Sup35 protein," *Science,* 289(5479):595-599 (2000).)

Li and Lindquist have shown that they can confer the SUP prion activity on an unrelated protein by genetically fusing portions of the SUP protein containing the peptide sequence 22-69. Thus, they demonstrated that the prion conferring characteristic of the SUP35 protein resides in the SUP 22-69 peptide. In analogy, the present invention is directed to a self-identifying peptide that causes aggregation. By grafting the sequence onto a protein (by conjugation) self aggregation can be conferred onto that protein: as a result, immediate precipitation of up to 95% of the Harlil protein conjugate at physiological pH is observed.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to identify several Harlil sequences of neural thread protein and determine their reactivity with NTP.

The following Harlil sequences were synthesized (Synpep, Dublin Calif.) and conjugated to maleimide activated Rabbit IgG (Jackson Immunoresearch, West Grove Pa.) and assessed for their NTP immunoreactivity. A linker was added, which is a repetition of the protein sequence occurring before and after the 90-96 H H A R L C L (portion of SEQ ID NO: 2) sequence of NTP. (SEQ ID NOS 4-11, respectively, in order of appearance)

| | | | | | | | | | | | | | | | | |
|---|---|---|---|---|---|---|---|---|---|---|---|---|---|---|---|---|
| 1. (NTP-1) | | | | | | L | H | A | R | L | C | L | A | N | F | C | G | R | N | R | V |
| 2. (NTP-2) | | | | | | | L | A | R | L | C | L | A | N | F | C | G | N | N | N | V |
| 3. (NTP-3) | | C | A | R | Y | R | T | G | H | H | A | R | L | M | | | |
| 4. (NTP-4) | | | | | | | H | H | A | R | L | P | L | A | N | F | C | G |
| 5. (NTP-5) | | | | | R | T | G | H | H | A | R | L | C*| L | A | N | F | C |
| 6. (NTP-6) | C | E | S | A | R | Y | R | T | G | H | H | A | R | L | C* | | |
| 7. (NTP-7) | | | | | | D | N | T | H | H | A | R | L | I | L | | |
| 8. (NTP-8) | | | | | | | S | H | H | A | R | L | I | L | | | |

*Blocked with Acetamido Methyl ($C_3H_6NO$).

Conjugation to carrier proteins was through a cysteine. Thus, peptides NTP-1 and NTP-2 produced mixed conjugate results because there is more than one cysteine residue. Therefore, for peptides NTP-5 and NTP-6, the secondary cysteine was blocked with ACM.

The location of the identified sequences in the NTP sequence is shown in FIG. 1. While all of the Harlil analogs showed some reactivity, NTP-3 was selected for most of the studies because it provided good reactivity while being easier to work with as it had a single cysteine residue.

As mentioned above, homologs and variants of the Harlil peptides are also encompassed by the scope of the invention. For construction of the homologous peptides of this example, homologous amino acids were used. The substitution criteria used were charge and/or size. Thus, the choice to substitute methionine for cysteine in NTP peptide 3 was based on overall similarity between these two amino acids and the desire to remove a reactive cysteine from this critical stretch of amino acids. The choice to substitute proline for cysteine was an attempt to see if this would mimic the conformational form of the peptide when it was in the protein and the cysteine was in disulfide linkage.

Other changes known to persons of skill in the art to affect or study affinity interactions include, but are not limited to, for example, interchanging leucine with other hydrophobic amino acids, such as isoleucine, valine, alanine or glycine; interchanging acidic amino acids or basic amino acids; interchanging histidine with phenylalanine to determine the effect of charge vs spatial; interchanging asparagine with aspartic, or glutamine with glutamic, to evaluate the effect of charge vs spatial; and interchanging serine with threonine, threonine with cysteine, aspartic with glutamic, arginine with lysine or histidine, and tyrosine with tryptophan or phenylalanine.

There appears to be no reason that the flanking sequences of NTP are required except as spacers, as only the Harlil peptide sequence has activity. The changes introduced to the flanking sequences were done to render the peptide less basic or hydrophobic.

EXAMPLE 2

The purpose of this example was to demonstrate the use of NTP-3 as an affinity ligand for affinity purification of NTP. In this process, NTP was purified on affinity column from a urine sample obtained from an AD patient.

Preparation of the Urine Sample Containing NTP for Testing: The biological source of NTP used was the urine of a patient (BOU1) diagnosed with AD. Before application to the column material, the biological sample was processed according to the following protocol for processing of urine for AD testing:

1. The urine was tested with an Ames Multistix™ (Bayer, Ind.). Samples are discarded if they: (a) are positive for bacterial contamination; (b) positive for pathologically high levels of protein, such as those associated with kidney disease (this test does not exclude samples positive for NTP lacking pathological levels of proteins), ketones, blood, urobilogen, nitrite, leucocytes; (c) have a pH greater than 7.5 or less than 4.5; or (d) have a specific gravity greater than 1.025.
2. The urine was centrifuged at 3000×g for 15 minutes to remove cellular debris.
3. The urine was filtered using a syringe through a 0.22 μm cellulose acetate filter, and the filtrate was brought to 0.05% azide.
4. The resultant aliquot was placed in the top reservoir of an Amicon Centricon® YM-10 Millipore, and centrifuged at 3000×g for one hour.
5. The sample, which was now about 25% of the original volume, was removed from the centrifuge and restored to the original volume with 1.5 mL of Tris Buffered Saline (TBS).
6. Steps 4 and 5 were repeated, in which the sample was centrifuged again at 3000×g for thirty minutes, followed by removal of the sample from the centrifuge, and 1.5 mL of TBS were added to the sample.
7. The sample was then centrifuged at 3000×g for thirty minutes, followed by removal of the sample from the centrifuge. The sample was then one fourth of the original volume.
8. The sample was then transferred to a borosilicate glass vial and stored frozen at −20° C.

Preparation of the column: NTP-3 was conjugated to cyanogen bromide-activated agarose (Sigma, St. Louis, Mo.) according to the manufacturer's directions. Once prepared, the column material was stored in 25 mM TRIS buffered saline (TBS), pH 7, with 0.01% azide.

Chromatography: 11 mL of the affinity column material was incubated for one hour with 25 mL of the urine sample (processed as described above to obtain a four times concentrated sample in TBS (pH 7)) and 25 mL of 0.025 M glycine buffer (pH 3.5). The unabsorbed material (pass through) was collected. The column was then washed with 5 volumes of 1×TBS (pH 7) and eluted in 11 mL of 0.1 M glycine (pH 2). Immediately following elution, the eluate was adjusted to pH 7 with NaOH, followed by concentration to 1 mL using an Amicon Centricon® YM-10 (Millipore, Beverly Mass.) as in Example 1.

Analysis of NTP Activity Present in the Affinity Column Eluate: Affinity assay activity was assayed using 7C Gold™ Strips, which test for neuronal thread protein in urine (Nymox Pharmaceutical Corp., Maywood N.J. See e.g., Fitzpatrick et al., *Alzheimer's Reports*, 3(3):155-159 (2000)). All activity as assayed by the 7C Gold™ strip was in the pH 2 eluate fraction.

Protein Concentration: The protein concentration in the eluate was 108 µg, as determined by Coomassie Blue staining (BioRad, Hercules, Calif.). This is about 3% of the starting protein concentration. Protein concentration was 145 µg, as determined by Bicinchoninic Acid Kit (Cat. # 23223, BioRad). Absorbance corrected for the buffer at 280 nm was 390, indicating 390 µg of protein. The larger protein amount obtained with absorbance measurement is likely a result of the presence of a large amount of aromatic amino acids in NTP, which can cause overestimation of protein using this measurement technique.

Analysis of the NTP Protein From the Affinity Column Eluate by Gel Electrophoresis: 1 µg of the eluate (approximately 110-145 ng) was run on a 12.5% sodium dodecyl sulfate (SDS) mini-gel (Amersham Pharmacia Biotech, Sweden) and stained with silver. Bands were observed at about 29 kD, 33 kD, 40-45 kD, and 60 kD. The gel was sliced into bands at 20-35 kD, 35-45 kD, and 45-65 kD and placed in 100 µl of TBS, and allowed to dialyze against the TBS overnight. The band eluates were then concentrated using an Amicon Centricon® YM-10, as in Example 1, and assayed for activity using the 7C Gold™ Assay.

NTP reactivity was observed in the 35-45 kD band, at about 41 kD. No activity was observed for the other bands. NTP has a reported molecular weight of 41 kD. Thus, the data indicate that the NTP-3 bound to the affinity column selectively bound the NTP protein present in the urine sample of the AD patient.

This example demonstrates the specific binding of the Harlil peptide NTP-3 to NTP, and the use of a Harlil peptide, such as NTP-3, as an affinity ligand for affinity purification of NTP.

EXAMPLE 3

The purpose of this example was to show the self-aggregation ability of a Harlil peptide. The Harlil peptide NTP-3 forms disulfide bonds (because of the cysteine residue) and dimerizes at neutral pH. Since the dimerized peptide can bind two immunoglobulins, it can cause precipitation. This property of Harlil peptides was demonstrated using rabbit immunoglobulin.

1 mg of the Harlil peptide NTP-3 in 1 mL of dimethylsulfoxide (DMSO) was added to 3.4 mg of rabbit IgG (Jackson Immunoresearch, West Grove, Pa.) at pH 7. The mixture was allowed to dialyze over night, and a clear white precipitate was observed the next morning. The precipitate was removed by centrifugation and the protein concentration of the supernatant was determined by absorbance at 280 nm using a Perkin Elmer spectrophotometer model Lambda 3B. The results are shown in Table 1. Precipitation of immunoglobulin is prevented at a low pH, e.g., pH of 3.5 or less 3.5.

TABLE 1

Immunoglobulin Precipitated Using a Harlil Peptide

| Starting Concentration | Final Concentration | % Protein Precipitated |
|---|---|---|
| 3.4 mg RGG* + 1 mg NTP-3 | 2.7 mg | 39% |

*rabbit IgG

This example demonstrates the ability of Harlil peptides to be used to isolate and/or purify immunoglobulins.

EXAMPLE 4

This example illustrates the usefulness of Harlil peptides in detecting and quantitating the presence of NTP.

Membrane Based Assay: The 7C Gold™ assay consists of a 5 mm×45 mm strip, with two traps and a sample receiving zone located on the strip. Traps 1 and 2 are located 16 and 24 mm distal from the sample receiving zone, respectively. Each trap is about 4 cm deep.

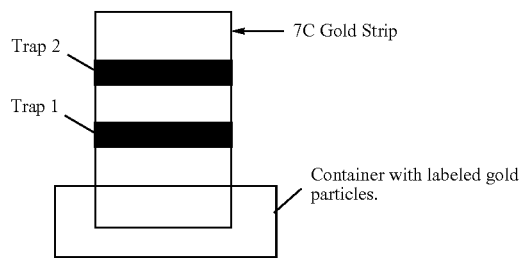

The labeled gold particles migrate to trap 1 or 2. The ratio of labeled gold in traps 1 and 2 correlates with the amount of NTP present in the sample. See U.S. Pat. No. 6,121,008

Preparation of NTP-3 Conjugate: Malemide activated rabbit immunoglobulin (RGG) (Pierce, Rockford, Ill.)) at a concentration of 3.8 mg/mL was brought to a pH of 3.5 using 1 M citrate. The Harlil peptide NTP-3, in DMSO at a 30 fold molar excess, was then added to the RGG. The NTP-3/RGG conjugate was monitored for pH and allowed to react overnight at room temperature with slow stirring. The conjugate was then thoroughly dialyzed against 0.5 mM, pH 3.5, citrate phosphate buffer.

Preparation of 7C Gold™ Strip Assay: The dialyzed NTP-3 conjugated to RGG was diluted to 1 mg/mL in 0.5 mM, pH 3.5, citrate phosphate buffer. After standing overnight, 6 µl/cm of the conjugate was coated on a membrane (Loprodyne 3, Pall, East Hills, N.Y.) using a XY3000™ Biodot (Irvine, Calif.) at Trap 1. Next, 0.5 mg/mL of goat anti-mouse immunoglobulin (DAKO #20109, Denmark) was coated on the membrane one centimeter above the NTP-3/RGG conjugate at Trap 2 (using the same parameters as the NTP-3/RGG coating). The membrane, or 7C Gold™ Strip, was hot aired dried for 30 minutes, cut into 5 mm strips, and stored with desiccant. This trap will bind anti-NTP-antibody coated gold in the absence of NTP. The 7C Gold™ assay uses an anti-NTP antibody N3I4 (de la Monte et al., J. of Neuropath. Exp. Neurol., 55:1038-1050 (1996)). The basis of this assay is that NTP is sequestered by the N3I4 anti-NTP antibody on gold and transported to the NTP-3 trap, where the NTP is competed off the N3I4 and binds to Trap 1. In doing so, the NTP blocks the binding of the antibody on the gold to trap 1 and, as a result, the gold migrates to Trap 2. Thus, in the presence of NTP more gold migrates to Trap 2.

Colloidal Gold: Colloidal gold was prepared as described in Colloidal Gold, M. A. Hayat ed. (Academic Press Limited, London (1991)), and coated with purified N3I4 anti-NTP antibody at a concentration of 20 µg/mL. The antibody-coated colloidal gold was then diluted into cryopreservative buffer (Serex Inc., Maywood, N.J.) and freeze dried. An amount sufficient for one strip was freeze dried in a 2 mL borosilicate vial (Wheaton #223683; Millville, N.J.) using a Virtus (Gardiner, N.Y.) Model 600SL & 12 SL freeze drier.

Patient Samples: 107 patient samples were processed and concentrated, as described in Example 2.

The 7C Gold™ Assay: 50 μl of each processed and concentrated patient sample was added to the NTP-antibody coated freeze dried gold. The mixture was incubated for 15 minutes at room temperature, following which the 7C Gold™ strip was placed in the vial until completion of the assay, as indicated by the appearance of a green line at the top of the strip. The strip was removed and allowed to dry.

Figure 3:
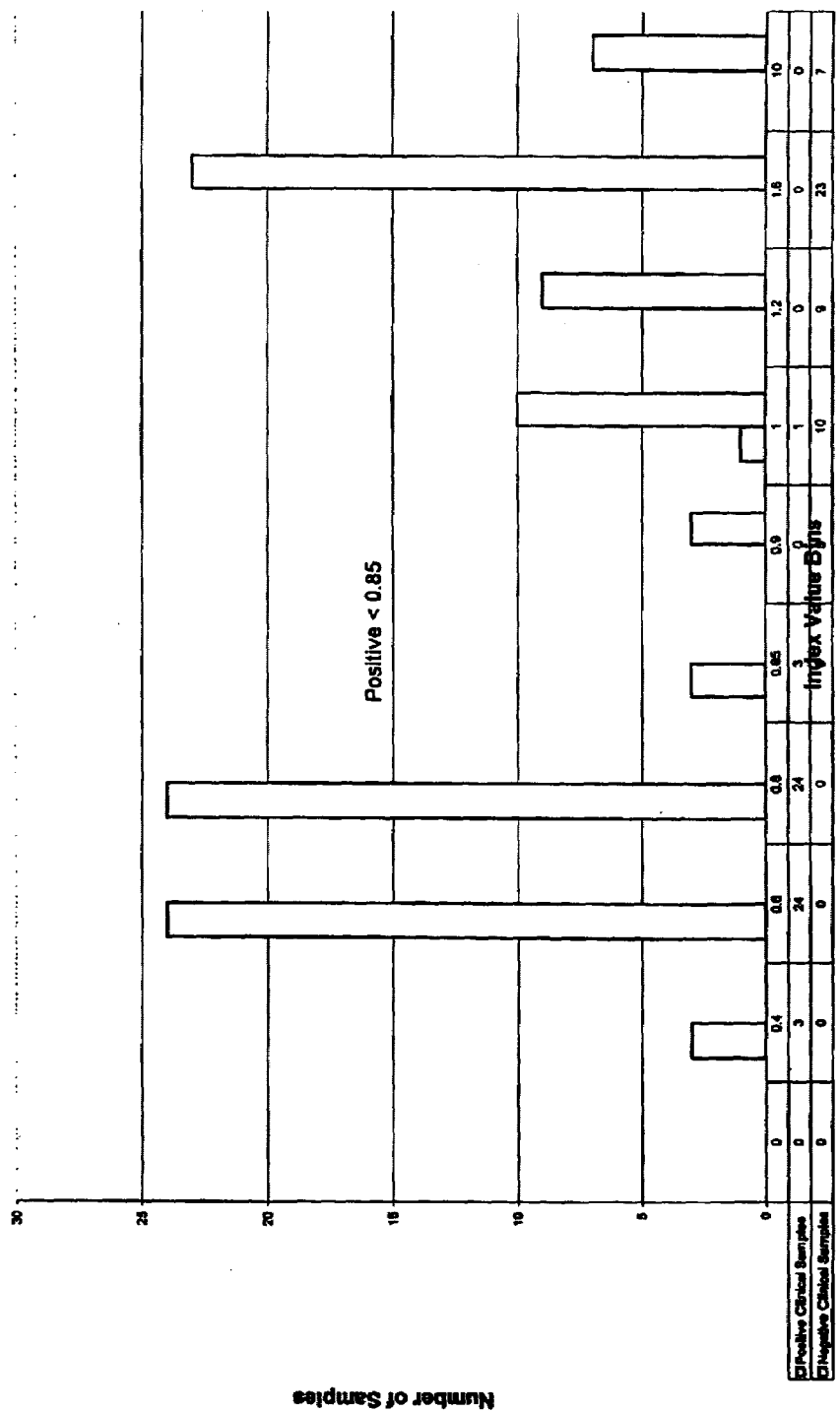
FIG. 3: Shows the results of assays of 107 biological samples using a Harlil peptide based membrane assay (data shown in Example 4)

Summary of Results: In the absence of NTP, most of the NTP antibody-coated gold binds to the Harlil peptide NTP-3 trap. The NTP Harlil peptide solid phase microtiter plate binds mouse antibody with very low affinity, but in its aggregated state on gold the N314 monoclonal antibody binds to the trap. The intensity of the color in bands one and two were then read using a densitometer (Gretag D19C, Switzerland). The Ratio Value, which is equal to Trap 1 reflectance divided by the reflectance in Trap 1 plus the reflectance in Trap 2, was calculated and the Ratio Value of the sample was divided by the ratio value of an index or cutoff sample. This value was designated the indexed value. The results of the assay, graphed in FIG. 3, show excellent separation of normal samples from AD samples.

EXAMPLE 5

The purpose of this example was to show that binding of NTP to a Harlil peptide coated microtiter plate could be inhibited by unconjugated Harlil peptide.

Preparation of Microtiter Plate: The Harlil peptide/immunoglobulin complex NTP3-RGG, in a ratio of 30:1 and prepared as in Example 4, was coated on an Immulon 4 microtiter plate (Dynex, Chantilly, Va.) at a concentration of 0.5 μg/well.

Standards: Recombinant NTP in TBS (described in de la Monte et al., *J. of Neuropath. Exp. Neurol.*, 55:1038-1050 (1996)). 0.01% azide (Nymox Pharm. Corp., Lot 4-7-98), was serially diluted into TBS. 100 μl of each dilution was incubated at pH 3.5 for one hour. The dilutions were then washed for fifteen minutes in TBS, 0.1% albumin, and 0.05% Tween 80. This was followed by 3 washes in TBS and 0.05% Tween 80.

Microtiter Plate Assay: 100 μl of 1:8000 dilution of peroxidase conjugated rabbit IgG (Jackson Immunoresearch, West Grove, Pa.) was then added and allowed to react for 30 minutes. The microtiter plate was washed twice with TBS and 0.05% Tween 80, followed by the addition of 150 μl of tetramethylbenzene (TMB) (Serex Inc., Maywood, N.J.). The mixture was then incubated for 10 min. and stopped with 50 μl of 2 N HCl. Absorbance was read in a SLT 340 ATTC spectrophotometer.

Using this system, it is shown that monomer NTP-3 inhibits the binding of conjugate to the plate. See FIG. 2.

EXAMPLE 6

The purpose of this example was to demonstrate that antibodies specifically bind to a Harlil peptide coated microtiter plate and to test what portion of the antibody (Fc or Fab) is binding to the Harlil coated plate.

Antibodies Tested: The following antibodies were obtained from Jackson Immunoresearch (West Grove, Pa.): (1) alkaline phosphate (AP) labeled affinity purified rabbit IgG anti-mouse antibody; (2) AP labeled affinity purified rabbit IgG anti-mouse (Fab2); and (3) AP labeled affinity purified rabbit IgG anti-chicken.

Rabbit IgG anti-chicken (antibody (3)) was used to eliminate the possibility that the rabbit anti-mouse (antibody (2)) was recognizing the RGG in the NTP-3/RGG conjugate. Antibody (2) was identical to Antibody (1), except that Antibody (2) lacked the Fc portion of the IgG.

Figure 4:
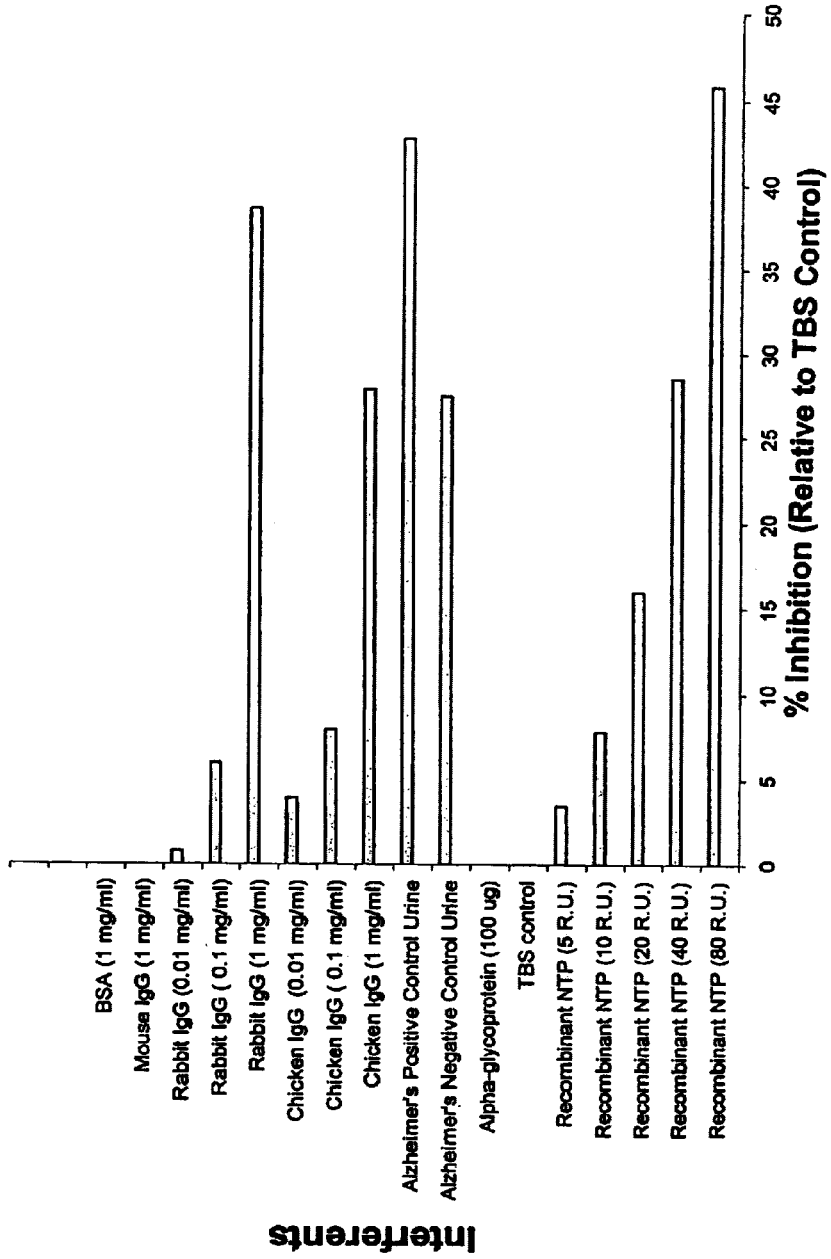
FIG. 4: Shows the results of an assay which determines the portion of an antibody to which NTP binds (data shown in Example 6)

The assay format was as in Example 5. Non-immune purified rabbit, chicken, and mouse IgG was added up to 1 mg/mL (see FIG. 4). Controls were 1 mg/mL BSA (bovine serum albumin), alpha-glycoprotein, AD positive and negative control urine, and 80, 40, 20, 10, and 5 units of Recombinant NTP. Both rabbit and chicken IgG competed off the AP conjugate in a dose-dependent manner. See FIG. 4. Fab2 did not bind to the plate.

Summary of Results: Both whole molecules, the rabbit anti-mouse and the rabbit anti-chicken, bound to a microtiter plate coated with NTP-3/rabbit IgG. The Fab labeled antibody did not exhibit any binding (results not shown). These results indicate that Harlil peptide antibody binding is effected through recognition of the antibody Fc region.

The affinity of Harlil peptides for IgG of different species varies. For example, mouse monoclonal antibody exhibited much lower affinity for the NTP-3 conjugates than did rabbit IgG. See FIG. 4.

EXAMPLE 7

The purpose of this example was to determine whether NTP recognizes the sequence in Protein G which recognizes the Fc portion of antibody.

Protein G binds antibody through the Fc region. Since the results of this example suggest that Harlil peptides also bind the Fc portion of immunoglobulins, and not the Fab portion, it was determined whether NTP recognizes the sequence in Protein G which recognizes the Fc portion of antibody. Specifically, since Harlil peptides recognize Harlil peptides, Harlil peptides recognize the Fc region of antibody, and Protein G recognizes the Fc region of antibody, this experiment determined whether Protein G recognizes NTP.

Both an NTP positive and an NTP negative sample were passed through a Protein G column. NTP was not significantly reduced. These results support the conclusion that Protein G does not bind to NTP.

Binding through the Fc region may have therapeutic implications, as the Fc region is used to recognize receptors in the immune system.

EXAMPLE 8

The purpose of this example was to demonstrate a competitive affinity assay in a microtiter plate assay format using a Harlil peptide.

Preparation of the Microtiter Plate. The Harlil peptide/immunoglobulin complex NTP-3/RGG, in a ratio of 30:1 and as prepared as in Example 4, was coated on an Immulon II microtiter plate (Dynex, Chantilly, Va.) at a concentration of 20 μg/well.

Preparation of Samples: Thirty urine samples were prepared for testing as described in Example 2. The filtrate was tested after the sample was spun in a 100 K Amicon Centricon (Millipore Inc., Beverly Mass.) to remove any antibody, as antibody Fc could interfere in the assay. (To prevent false positives in diagnostic tests, the ability of a Harlil peptide to bind non-NTP antibodies is disabled. For example, samples having immunoglobulin levels greater than 100 μg/mL must have immunoglobulin levels reduced to less than 100 μg/mL prior to assay.)

Controls: A urine pool prepared from urine of individuals with no diagnosis of any neurodegenerative diseases was passed over an affinity column, prepared as described in Example 2. The resultant urine pool is referred to as "stripped" urine.

Stripped urine was then used to prepare a mid range control by appropriate dilution of a high pool. The high pool was prepared from a collection of samples from patients diagnosed with AD who tested positive in the assay for NTP (see Example 4).

Figure 5:
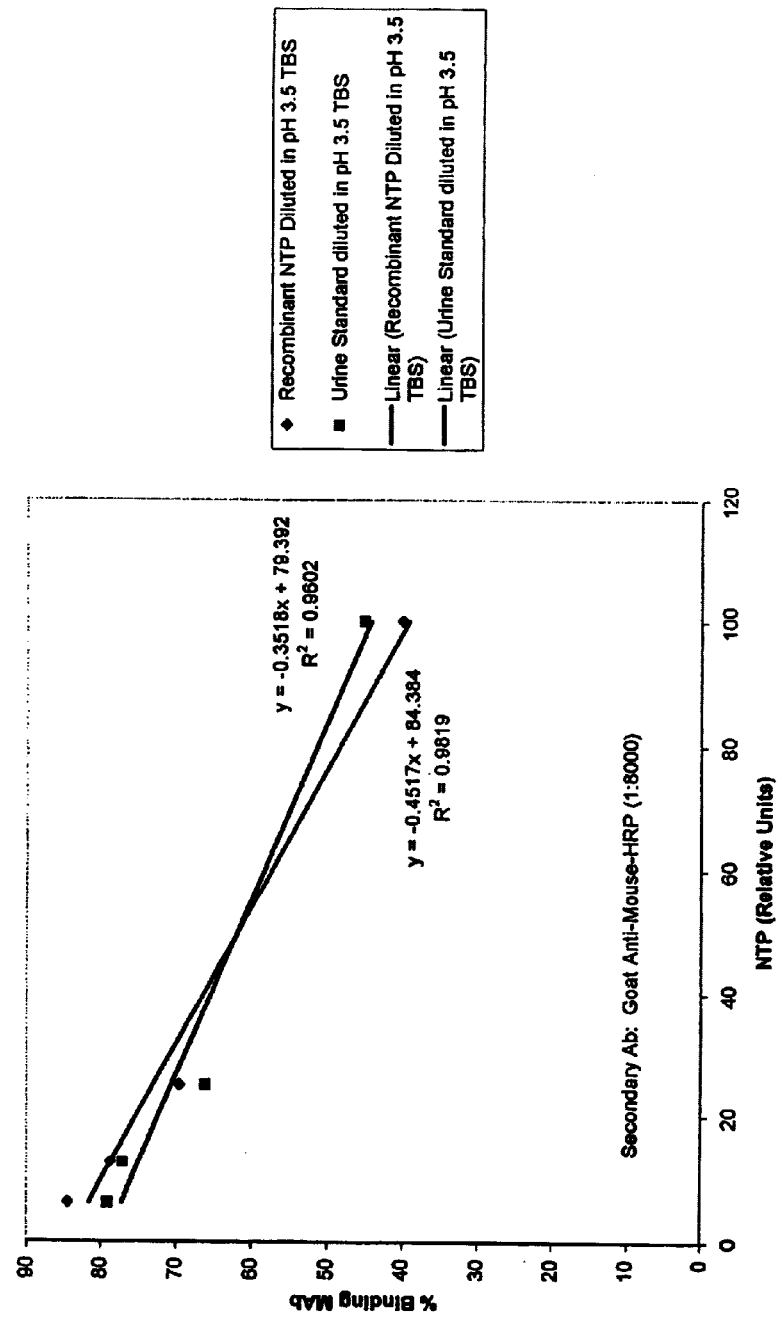
FIG. 5: Compares the linearity of a urine control sample and recombinant NTP in an ELISA format competitive NTP assay (data shown in Example 8)

Standards. Recombinant NTP (Nymox Pharmaceutical Corp, Montreal Canada) was diluted into TBS to form standards. Standards were assigned unit values of 40, 20, 10, and 0. Because there is evidence that NTP in urine may be partially degraded, the amount of NTP was expressed in Recombinant NTP units and not in weight. FIG. 5 compares the linearity of a urine control sample and recombinant NTP in a microtiter format competitive NTP assay.

The Assay. Patient samples were tested in the assay as follows: 50 μl of a 1:5000 dilution of peroxidase conjugated rabbit IgG (Jackson Immunoresearch, West Grove, Pa.) and 50 μl of sample or standard was added to the wells of the plate. The plate was incubated at 1 hour at room temperature, and then washed three times in TBS, 0.1% albumin, and 0.05% Tween 80. 100 μl of PNPP (Para Nitro Phenyl Phosphate) (Moss, Pasadena, Md.) was added to each well. The OD at 405 nm was read on a BioRad Reader at 30 minutes and thereafter at fifteen minute intervals until the OD of TBS standard was between 2-2.5. The results, shown in FIG. 6, demonstrate that while NTP is found in all samples, there is an elevated amount present in AD-positive patients. This elevated amount can easily be determined using age-matched controls. Thus, a diagnostic test which determines the amount of NTP in a biological sample can be useful in the diagnosis of AD or other neurodegenerative disorder with high accuracy.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An isolated peptide that does not exceed 25 amino acids in length wherein:
   (a) said peptide contains the amino acid sequence H A R L (portion of SEQ ID NO:2, residues 292-295); and
   (b) optionally contains additional amino acids before and after the amino acid sequence H A R L of said peptide wherein said peptide has 100% homology to a Neural Thread Protein (NTP) sequence.

2. The isolated peptide of claim 1, wherein the peptide consists of the amino acid sequence H A R L (portion of SEQ ID NO:2, residues 292-295).

3. An isolated peptide comprising a fragment of a Neural Thread Protein (NTP) sequence, wherein said fragment comprises the amino acid sequence H A R L, and wherein said peptide does not exceed 25 amino acids in length.

* * * * *